United States Patent
Wouhaybi et al.

(10) Patent No.: US 10,602,599 B2
(45) Date of Patent: Mar. 24, 2020

(54) TECHNOLOGIES FOR ANALYZING LIGHT EXPOSURE

(71) Applicant: Intel Corporation, Santa Clara, CA (US)

(72) Inventors: Rita H. Wouhaybi, Portland, OR (US); Igor Tatourian, Santa Clara, CA (US); Hong Li, El Dorado Hills, CA (US); Lama Nachman, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 105 days.

(21) Appl. No.: 14/979,120

(22) Filed: Dec. 22, 2015

(65) Prior Publication Data

US 2017/0181252 A1    Jun. 22, 2017

(51) Int. Cl.
| | |
|---|---|
| *H05B 37/02* | (2006.01) |
| *H05B 47/175* | (2020.01) |
| *H05B 47/11* | (2020.01) |
| *H05B 47/105* | (2020.01) |

(52) U.S. Cl.
CPC ......... *H05B 47/175* (2020.01); *H05B 47/105* (2020.01); *H05B 47/11* (2020.01); *Y02B 20/46* (2013.01)

(58) Field of Classification Search
CPC .............. H05B 3/0245; H05B 37/0218; H05B 37/0227; G05B 15/02
USPC ........................................................ 700/275
See application file for complete search history.

(56) References Cited

U.S. PATENT DOCUMENTS

| | | | |
|---|---|---|---|
| 2006/0055666 A1 | 3/2006 | Chong et al. | |
| 2008/0260242 A1 | 10/2008 | Mackinnon et al. | |
| 2010/0301776 A1* | 12/2010 | Feri | H05B 37/0272 315/312 |
| 2015/0022093 A1 | 1/2015 | Smith et al. | |
| 2015/0048742 A1* | 2/2015 | Wingren | H05B 37/0218 315/152 |
| 2015/0156388 A1 | 6/2015 | Neglur | |
| 2015/0238774 A1* | 8/2015 | Anderson | A61F 13/00063 604/20 |
| 2016/0316543 A1* | 10/2016 | Liu | F21V 21/26 |

OTHER PUBLICATIONS

International search report for PCT application No. PCT/US2016/063335, dated Jan. 18, 2017 (3 pages).
Written opinion for PCT application No. PCT/US2016/063335, dated Jan. 18, 2017 (8 pages).

* cited by examiner

*Primary Examiner* — Robert A Cassity
(74) *Attorney, Agent, or Firm* — Barnes & Thornburg LLP

(57) ABSTRACT

Technologies for light exposure analysis include a computer configured to collect light data of an environment and a remote computer communicatively coupled to the computer. The remote computer is configured to receive/retrieve health information for one or more users and analyze the health information to generate a health profile for each of the one or more users. Additionally, the remote computer is configured to determine whether any correlations exist between the health profiles and the light data. The remote computer is further configured to analyze the collected light data against one or more health profiles to determine a desired lighting condition for a user based at least in part on the correlations between the health profiles and the light data. Other embodiments are described and claimed.

20 Claims, 5 Drawing Sheets

TECHNOLOGIES FOR ANALYZING LIGHT EXPOSURE

BACKGROUND

Light is commonly held to be essential to life, be the life human, animal, or plant-based. However, natural light (i.e., the portion of the electromagnetic radiation given off by the sun) faces any number of impediments, including the atmosphere, the setting of the sun, landforms, man-made structures, etc. Plants are especially sensitive to lighting conditions. As such, grow lights, or plant lights, have been developed to provide an artificial light source similar to the light spectrum of the sun to stimulate plant growth where there is no naturally occurring light, or where supplemental light is required.

As such, artificial lighting has been used to provide illumination where natural light cannot, as well as in conditions in which the artificial lighting is complementary to natural lighting. Artificial light is composed of visible light, as well as ultraviolet and infrared radiations. Various forms of artificial lighting include incandescent light bulbs, fluorescent tubes, light-emitting diodes, etc., to produce visible light.

Sensitivity to light in humans, medically referred to as photophobia, is a symptom of abnormal intolerance to visual perception of light. Such exposure to natural light and/or artificial light can be felt as an experience of discomfort or pain to the eyes due to light exposure. Additionally, sensitivity to light can be a symptom of underlying diseases that don't directly affect the eyes (e.g., viral illness, headaches, etc.). As a result of the proliferated use of artificial lighting, concern exists that the emission levels of some artificial light sources could be harmful to the skin and/or the eyes. Both natural light and artificial light can disrupt the human body clock and the hormonal system, which can lead to health problems.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
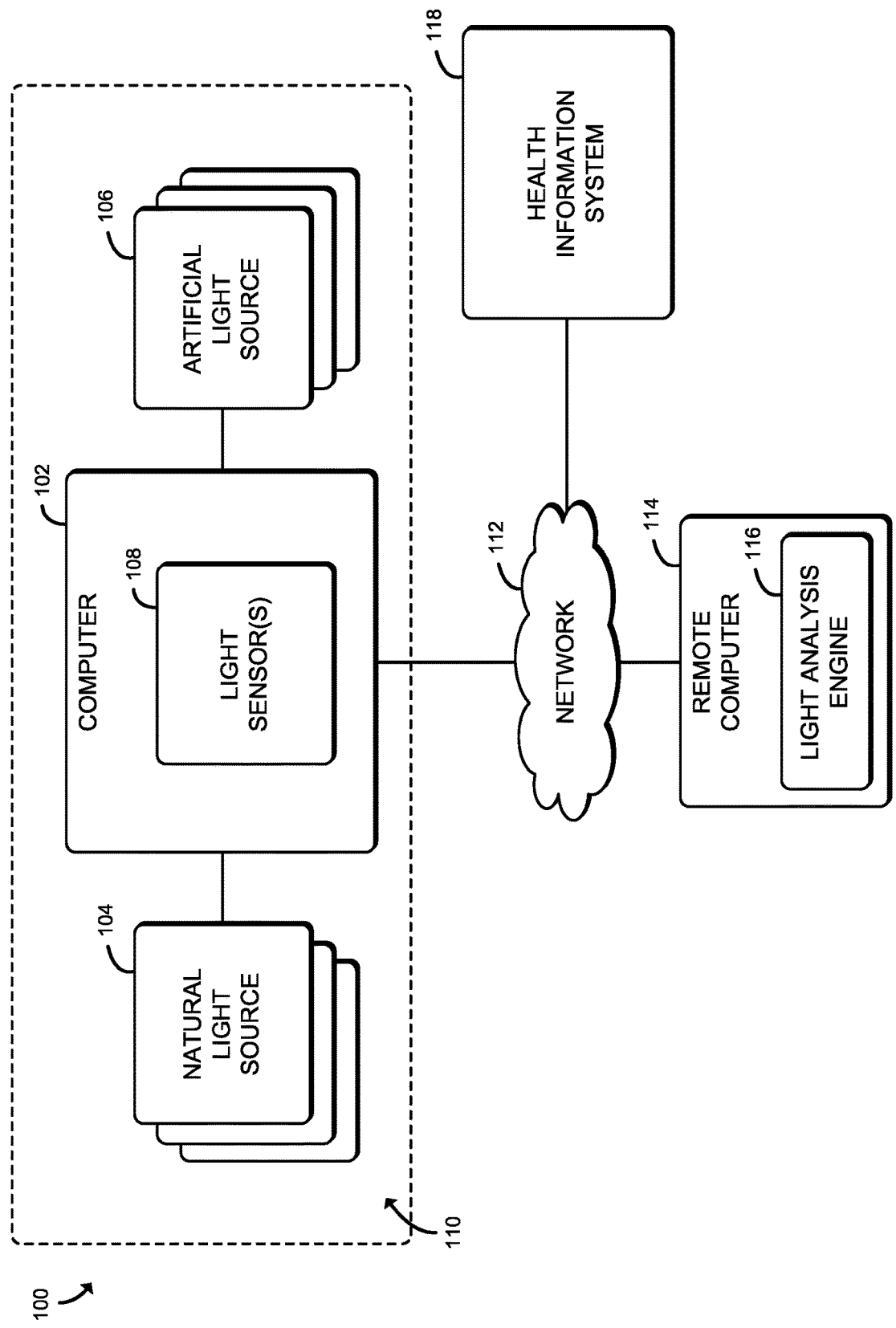
FIG. 1 is a simplified block diagram of at least one embodiment of a system for analyzing light exposure of an environment.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Additionally, it should be appreciated that items included in a list in the form of "at least one of A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a system 100 for analyzing light exposure includes a computer 102 communicatively coupled to a remote computer 114 over a network 112. The remote computer 114 is further communicatively coupled to a health information system 118 via the network 112. In use, the computer 102 detects one or more natural light sources 104 and/or one or more artificial light sources 106 of an environment 110 via one or more light sensors 108 of the computer 102. The computer 102 is configured to transmit the light data collected by the light sensor(s) 108 and/or data derived therefrom) to the remote computer 114. While only a single computer 102 is shown in the illustrative environment 110, it should be appreciated that more than one computer 102 may be present in other embodiments.

The health information system 118 is configured to store electronic medical records (EMRs) that include health information of patients, such as identifying information, health symptoms, administered treatments, and outcomes, for example. Accordingly, the health information system 118 may be used by a healthcare facility (e.g., a hospital) to track patient records. The health information system 118 is further configured to transmit at least a portion of the health information to the remote computer 114.

The illustrative remote computer 114 includes a light analysis engine 116 that is configured to receive and interpret the light data from the computer 102 and the health information from the health information system 118. As will be described in further detail below, the light analysis engine 116 of the remote computer 114 is further configured to determine correlations between the light data and the health information, which can be used to generate recommendations and/or actions associated with adjusting light exposure for a particular user (e.g., a user of the computer 102). It should be appreciated that the light analysis engine 116 may be configured to combine at least a portion of the light data and/or the health information for different users, such that the combined light data and/or health information may be analyzed to produce results usable to influence the recommendations and/or actions associated with adjusting light exposure for a particular user.

The computer 102 may be embodied as any type of compute device that is capable of performing the functions described herein, such as, without limitation, a portable computing device (e.g., smartphone, tablet, laptop, notebook, wearable, etc.) that includes mobile hardware (e.g., processor, memory, storage, wireless communication circuitry, etc.) and software (e.g., an operating system) to support a mobile architecture and portability, a personal computer, a household appliance, a home entertainment unit, a distributed computing system, a processor-based system, a multiprocessor system, and/or any other computing/communication device.

Figure 2:
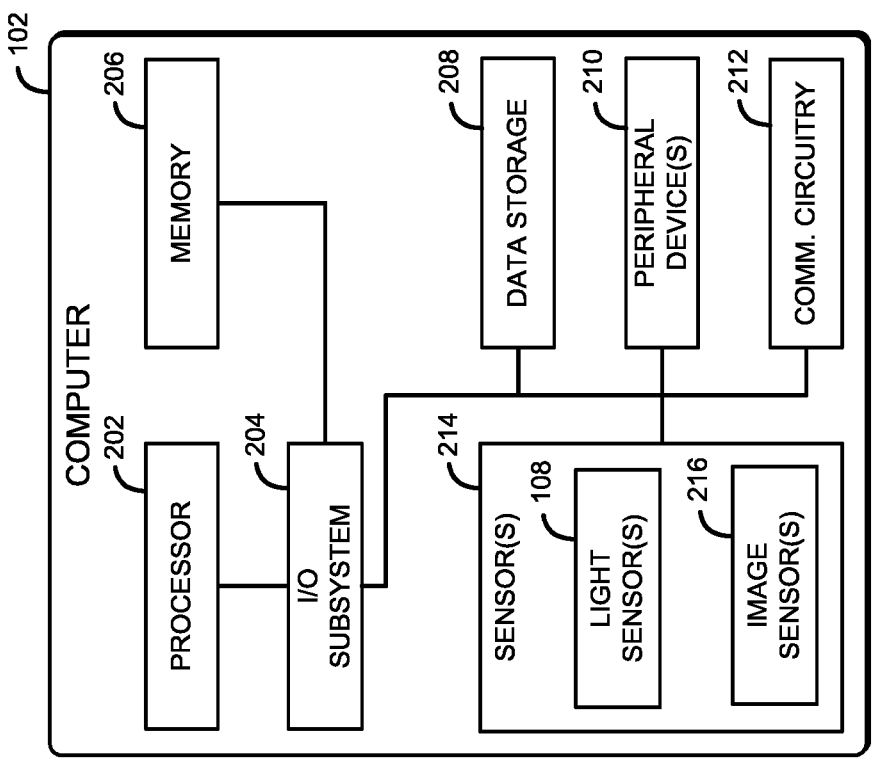
FIG. 2 is a simplified block diagram of at least one embodiment of a computer of the system of FIG. 1.

As shown in FIG. 2, the illustrative computer 102 includes a processor 202, an input/output (I/O) subsystem 204, a memory 206, a data storage device 208, one or more peripheral devices 210, communication circuitry 212, and various sensors 214, including the light sensors 108 of FIG. 1. Of course, in other embodiments, the computer 102 may include other or additional components, such as those commonly found in a computing device. Additionally, in some embodiments, one or more of the illustrative components may be incorporated in, or otherwise form a portion of, another component. For example, the memory 206, or portions thereof, may be incorporated in the processor 202 in some embodiments. Further, in some embodiments, one or more of the illustrative components may be omitted from the computer 102.

The processor 202 may be embodied as any type of processor capable of performing the functions described herein. For example, the processor 202 may be embodied as a single or multi-core processor(s), digital signal processor, microcontroller, or other processor or processing/controlling circuit. The memory 206 may be embodied as any type of volatile or non-volatile memory or data storage capable of performing the functions described herein. In operation, the memory 206 may store various data and software used during operation of the computer 102, such as operating systems, applications, programs, libraries, and drivers.

The memory 206 is communicatively coupled to the processor 202 via the I/O subsystem 204, which may be embodied as circuitry and/or components to facilitate input/output operations with the processor 202, the memory 206, and other components of the computer 102. For example, the I/O subsystem 204 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 204 may form a portion of a system-on-a-chip (SoC) and be incorporated, along with the processor 202, the memory 206, and/or other components of the computer 102, on a single integrated circuit chip.

The data storage device 208 may be embodied as any type of device or devices configured for short-term or long-term storage of data, such as memory devices and circuits, memory cards, hard disk drives, solid-state drives, or other data storage devices, for example. It should be appreciated that the data storage device 208 and/or the memory 206 (e.g., the computer-readable storage media) may store various types of data capable of being executed by a processor (e.g., the processor 202) of the computer 102, including operating systems, applications, programs, libraries, drivers, instructions, etc.

The peripheral devices 210 may include any number of input/output devices, interface devices, and/or other peripheral devices. For example, in some embodiments, the peripheral devices 210 may include a display, a touch screen, graphics circuitry, a keyboard, a mouse, a microphone, a speaker, and/or other input/output devices, interface devices, and/or peripheral devices. The particular devices included in the peripheral devices 210 may depend on, for example, the type and/or intended use of the computer 102. The peripheral devices 210 may additionally or alternatively include one or more ports, such as a USB port, for example, for connecting external peripheral devices to the computer 102.

The communication circuitry 212 may be embodied as any communication circuit, device, or collection thereof, capable of enabling communications between the computer 102 and other computers (e.g., the remote computer 114) over a network (e.g., the network 112). For example, the communication circuitry 212 may include a network interface controller (NIC) (not shown) and/or other devices capable of performing network communication-related operations. The communication circuitry 212 may be configured to use any one or more wired or wireless communication technologies and associated protocols (e.g., Ethernet, Wi-Fi®, Bluetooth®, Bluetooth® Low Energy (BLE), near-field communication (NFC), Worldwide Interoperability for Microwave Access (WiMAX), etc.) to affect such communication. The communication circuitry 212 may be additionally configured to use any one or more wireless and/or wired communication technologies and associated protocols to effect communication with other computing devices, such as over a network, for example.

The sensors 214 may be embodied as any type of circuitry, hardware, software, or combination thereof capable of performing the functions described herein. The illustrative sensors 214 includes the one or more light sensors 108 (e.g., a visible light sensor, an invisible light sensor, etc.) and one or more image sensors 216 (e.g., an image sensor array). The light sensors 108 may be embodied any type of photosensor, or photodetector, capable of sensing light and/or other electromagnetic energy. In some embodiments, one or more of the light sensors 108 may be configured to sense light of a particular wavelength or range of wavelengths. The image sensors 216 may be embodied as or otherwise include one or more charge-coupled device (CCD) image sensors, complementary metal-oxide-semiconductor (CMOS) image sensors, and/or any type of image sensor capable of performing the functions described herein.

It should be appreciated that the sensors 214 may include additional and/or alternative sensors commonly found in a computer, such as depth sensor(s) usable to estimate depths of objects in a field of view of the sensors 214, motion detecting sensor(s) capable of detecting a motion of the sensors 214 and/or detecting a motion in proximity to the sensors 214, etc. It should be further appreciated that the sensors 214 may additionally include other sensors not commonly found in a computer, such as various biometric feedback sensors, including biosignal sensors to sense electrical resistance (e.g., a galvanic skin response), skin moisture or temperature, or magnetic fields (e.g., a Magnetoencephalogram, or MEG), while still other biometric feedback sensors may be used for neuro-vascular coupling (e.g., a functional near-infrared spectroscopy, or fNIR) to sense blood flow.

Referring back to FIG. 1, the network 112 may be embodied as any type of wired or wireless communication network, including a wireless local area network (WLAN), a wireless personal area network (WPAN), a cellular network (e.g., Global System for Mobile Communications (GSM), Long-Term Evolution (LTE), etc.), a telephony network, a digital subscriber line (DSL) network, a cable network, a local area network (LAN), a wide area network (WAN), a global network (e.g., the Internet), or any combination thereof. It should be appreciated that, in such embodiments, the network 112 may serve as a centralized network and, in some embodiments, may be communicatively coupled to another network (e.g., the Internet). Accordingly, the network 112 may include a variety of other network computing devices (e.g., virtual and physical routers, switches, network hubs, servers, storage devices, compute devices, etc.), as needed to facilitate communication between the computer 102 and the remote computer 114, as well as the remote computer 114 and the health information system 118.

Figure 3:
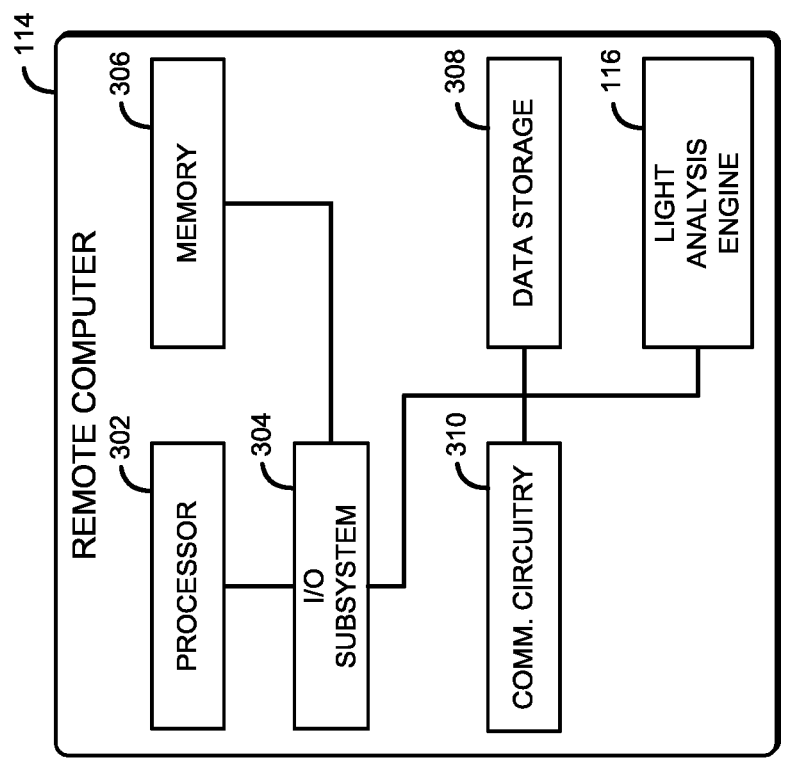
FIG. 3 is a simplified block diagram of at least one embodiment of a remote computer of the system of FIG. 1.

The remote computer 114 may be embodied as any type of compute device capable of performing the functions described herein, including, without limitation, a server (e.g., stand-alone, rack-mounted, blade, etc.), a network appliance (e.g., physical or virtual), a switch (e.g., rack-mounted, standalone, fully managed, partially managed, full-duplex, and/or half-duplex communication mode enabled, etc.), a router, a web appliance, a personal computer, a distributed computing system, a processor-based system, and/or a multiprocessor system. As shown in FIG. 3, similar to the illustrative computer 102, the illustrative remote computer 114 includes a processor 302, an I/O subsystem 304, a memory 306, a data storage device 308, and communication circuitry 310, as well as the light analysis engine 116 of FIG. 1. As such, further descriptions of the like components are not repeated herein with the understanding that the description of the corresponding components provided above in regard to the computer 102 applies equally to the corresponding components of the remote computer 114.

The light analysis engine 116 may be embodied as any circuitry, hardware, software, or collection thereof, capable of performing the functions described herein, including augmenting received light data with received health information, performing an analysis on the light data and the health information, and determining correlations between the light data and the health information based on the analysis. The light data may include any data indicative of natural and/or artificial light, or a quality thereof, which may be collected in the environment 110 in which the computer 102 is being operated.

Additionally, the light analysis engine 116 is configured to identify and extract patterns based on the determined correlations, as well as generate light exposure recommendations based on the present light conditions of the environment 110, health information of an occupant of the environment 110, and the identified patterns. In some embodiments, the light analysis engine 116 may form a portion of the processor 302 or otherwise may be established by the processor 302. In other embodiments, the light analysis engine 116 may be embodied as an independent circuit or processor (e.g., a specialized co-processor or application specific integrated circuit (ASIC)).

Referring again to FIG. 1, the health information system 118 may be embodied as any one or more types of compute devices capable of capturing, storing, managing, and/or transmitting health related information of patients input into the health information system 118, including, without limitation, a server (e.g., stand-alone, rack-mounted, blade, etc.), a network appliance (e.g., physical or virtual), a switch (e.g., rack-mounted, standalone, fully managed, partially managed, full-duplex, and/or half-duplex communication mode enabled, etc.), a router, a web appliance, a personal computer, a portable computing device (e.g., smartphone, tablet, laptop, notebook, wearable, etc.), a distributed computing system, a processor-based system, and/or a multiprocessor system. As described previously, the health information may include any data relating to the health of a patient, such as information identifying the patient, health symptoms, treatments administered on the patient based on the health symptoms, patient outcomes that resulted from the administered treatments, etc.

Figure 4:
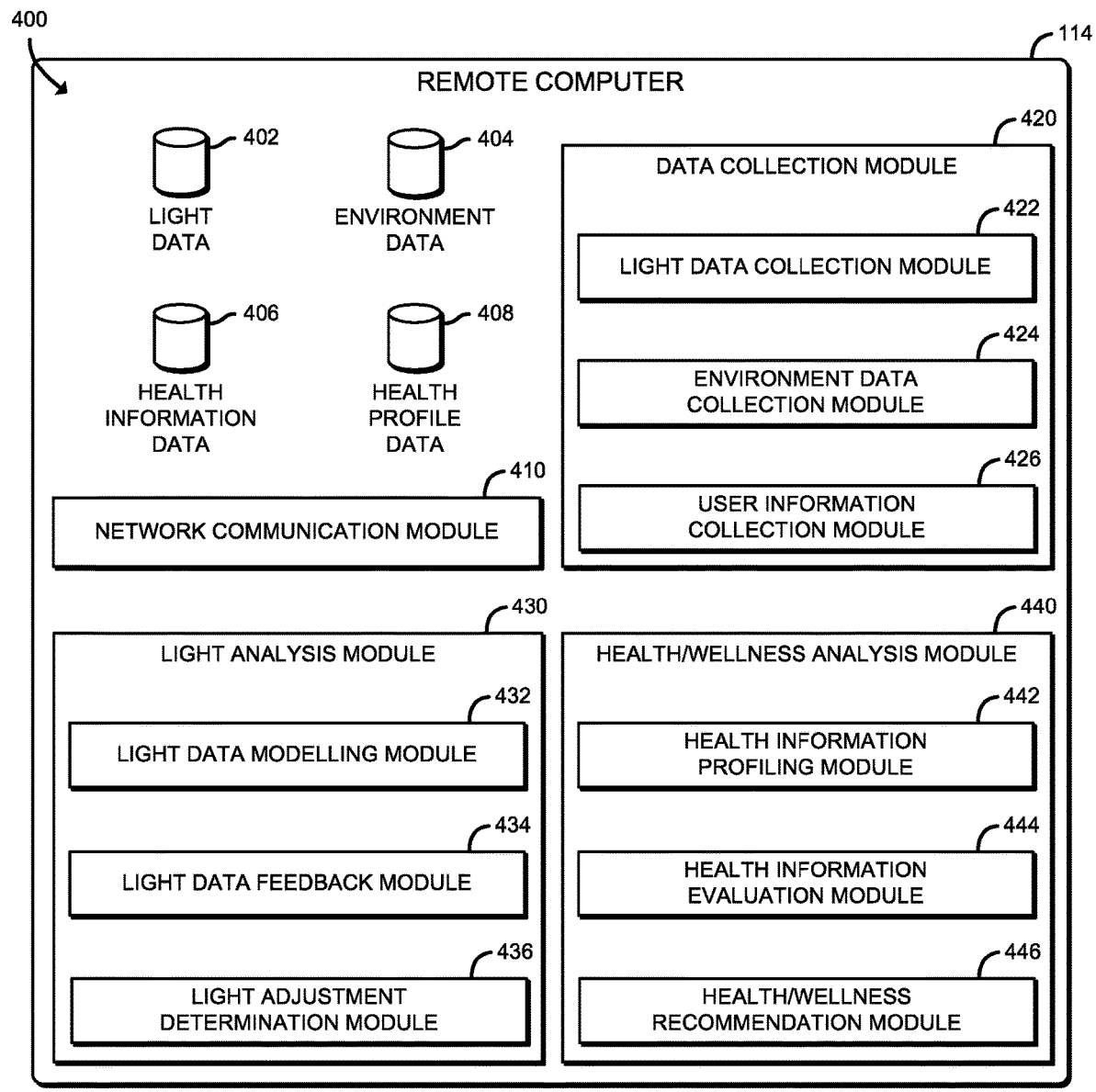
FIG. 4 is a simplified block diagram of at least one embodiment of an environment of the remote computer of FIG. 3.

Referring now to FIG. 4, in an illustrative embodiment, the remote computer 114 establishes an environment 400 during operation. The illustrative environment 200 includes a network communication module 410, a data collection module 420, a light analysis module 430, and a health/wellness analysis module 440. Each of the modules, logic, and other components of the environment 400 may be embodied as hardware, software, firmware, or a combination thereof. For example, each of the modules, logic, and other components of the environment 400 may form a portion of, or otherwise be established by, the processor 302, the memory 306, the communication circuitry 310, and/or other hardware components of the remote computer 114. As such, in some embodiments, one or more of the modules of the environment 400 may be embodied as circuitry or a collection of electrical devices (e.g., network communication circuitry 410, data collection circuitry 420, light analysis circuitry 430, and health/wellness analysis circuitry 440, etc.).

In the illustrative environment 400, the remote computer 114 includes light data 402, environment data 404, health information data 406, and health profile data 408, each of which may be stored in the memory 306 and/or the data storage device 308 of the remote computer 114, and may be accessed by the various modules and/or sub-modules of the remote computer 114. It should be appreciated that the remote computer 114 may include additional and/or alternative components, sub-components, modules, sub-modules, and/or devices commonly found in a computing device, which are not illustrated in FIG. 4 for clarity of the description.

The network communication module 410 is configured to facilitate inbound and outbound wired and/or wireless network communications (e.g., network traffic, network packets, network flows, etc.) to and from the remote computer 114. To do so, the network communication module 410 is configured to receive and process network packets from other computing devices (e.g., the computer 102, the health information system 118, and/or other computing device(s) communicatively coupled to the remote computer 114). Additionally, the network communication module 410 is configured to prepare and transmit network packets to another computing device (e.g., the computer 102, the health information system 118, and/or other computing device(s) communicatively coupled to the remote computer 114).

The data collection module 420 is configured to collect and aggregate data received at the remote computer 114 for analysis. To do so, the illustrative data collection module 420 includes a light data collection module 422, an environment data collection module 424, and a user information collection module 426. The light data collection module 422 is configured to receive light-related data from the computer 102, as described above. The light-related data may include any data associated with a characteristic of the light perceived by the computer 102 (i.e., the light sensor 108), including an intensity level, a type of light, a sample of light at varying frequencies, a capability (e.g., a wattage range, a lumens range, etc.), a present wattage value, a present lumens value, a calibration setting of the light sensor 108, whether the light sensor 108 is obstructed, a distance an obstruction is from the light sensor 108, a position of the light sensor 108, an angle of the light sensor 108, an ambient light value, a reflected light value, etc.

It should be appreciated that one or more characteristics of the light may be determined from one or more other sensors of the computer 102, such as the image sensor(s) 216. It should be further appreciated that light data may be received by the remote computer 114 from light emitting sources capable of reporting characteristics of their operation (e.g., connected light bulbs). In some embodiments, the light-related data may be stored in the light data 402.

The environment data collection module 424 is configured to receive environment-related data from the computer 102. The environment data may include any type of data of the environment (e.g., the environment 110) of the computer 102 at the time at which light data was transmitted to the remote computer 114 and/or the user at the computer, such as a time of day, a timezone, a date, a geo-location, an elevation, a humidity level, etc. It should be appreciated that one or more characteristics of the environment data may be determined from one or more sensors of the computer 102, such as the image sensor(s) 216 (e.g., for observing change of state of the environment 110 and/or an object of the environment 110) which may be used to capture an image of the environment and/or the user from which analysis thereof may provide additional environment data. As such, the environment data may additionally include any type of data related the user at the computer 102, such as a gesture (e.g., the user covering their eyes), a reaction (e.g., the user squinting), etc., that may be determined from the image of the environment and/or the user. In some embodiments, the environment-related data may be stored in the environment data 404.

The user information collection module 426 is configured to receive/retrieve health information. As described above, the health information may include any data relating to health and well-being (physical and/or mental), including identifying information, health symptoms, treatments administered based on the health symptoms, outcomes from the administered treatments, etc. Accordingly, in some embodiments, the user information collection module 426 may be configured to receive/retrieve health-related information of a number of patients and user profile data of the people being analyzed, such as via digital medical records from a health information system (e.g., the health information system 118 of FIG. 1).

Additionally or alternatively, in some embodiments, the health information may include wellness information, which may be input directly from the user, such as wellness information relating to height, weight, diet, exercise, vitamins, sleep, mood, etc. As such, in some embodiments, the user information collection module 426 may be configured to receive/retrieve health information directly from a user, such as via a network-connected computer (e.g., the computer 102) communicatively coupled to the remote computer 114. In some embodiments, the health and/or wellness information may be stored in the health information data 406.

The light analysis module 430 is configured to analyze light-related data, such as may be stored in the light data 402. To do so, the light analysis module 430 includes a light data modelling module 432 that is configured to model historical and/or present light data and make various measurements based on the models. It should be appreciated that the light analysis module 430 may be configured to use any known techniques, machine learning algorithms, and physical laws for modelling the light data. The light analysis module 430 is further configured to analyze light data to provide recommendations based on the analyzed light related data and/or determine one or more desired lighting conditions for a particular environment (e.g., the environment 110 of FIG. 1). To do so, the illustrative light analysis module 430 additionally includes a light data feedback module 434 and a light adjustment determination module 436.

The light data feedback module 434 is configured to provide different views of light data, such as visual displays of the fusion energy of light elements of an environment, histograms, heat maps, text-based lighting condition values, etc., based on the environment in which the light data has been collected. In other words, the light data feedback module 434 is configured to when, where, and what kind of light a person, a plant, an animal, a work or art, a picture a document, etc., is exposed to at any given time, historically and/or presently.

The light data feedback module 434 is further configured to receive response input from a user, such that one or more desired lighting settings may be determined from the feedback/response. The desired lighting settings may include any light settings related a characteristic of the light perceived by the computer 102 (i.e., the light sensor 108), including an intensity level of light emitted, a type of light emitted, a capability setting (e.g., a wattage range, a lumens range, etc.), a wattage value setting, a lumens value setting, a calibration setting of the light sensor 108, a position of the light sensor 108, an angle of the light sensor 108, an state (i.e., on/off) of the light, etc. It should be appreciated that the desired lighting settings may be different based on the type of computer 102, the user, the environment 110, etc.

The light adjustment determination module 436 is configured to interpret the analyzed data and any other additional input data to determine whether any light adjustments (e.g., notifications, automatically performed actions, etc.) are recommended. For example, for a user with light sensitivity, the light adjustment determination module 436 may be configured to analyze environments where the user is presently, such as may be determined via global positioning system coordinates received from a portable computer worn by the user, and/or where it expects the user to be in the future, such as may be determined based on input from a user via a computer of the user, reservations made online using the user's computer, a map application being executed on the user's computer, etc. Accordingly, the light adjustment determination module 436 may be configured to warn the user a present condition of the environment and/or pre-emptively warn the user before entering into an environment having a particular lighting condition that may cause the user discomfort.

In another example, in a plant growing environment, the light adjustment determination module 436 may be configured to determine a present lighting condition for an environment 110, a portion of the environment 110, and/or a particular source of light. The present lighting condition includes one or more present lighting properties that define the present lighting condition, such as an amount of light being emitted from a particular light source (e.g., a natural or artificial light source), an amount of light detected by the computer 102 (e.g., by the one or more light sensors 108 of the computer), a type of light source, a present setting of a light source, etc., in the environment 110. Accordingly, the light adjustment determination module 436 may be configured to determine any other light condition threshold is being met, such as determining whether an optimal level of light is being emitted within the environment, at a group of plants, at a single plant, etc.

In still another example, in an office environment, the light adjustment determination module 436 may be configured to determine a present lighting condition for an environment 110, a portion of the environment 110, and/or a particular source of light. As described previously, the present lighting condition includes one or more present lighting properties that define the present lighting condition, such as an amount of light being emitted from a particular light source (e.g., a natural or artificial light source), an amount of light detected by the computer 102 (e.g., by the one or more light sensors 108 of the computer), a type of light source, a present setting of a light source, etc., in the environment 110. Accordingly, the light adjustment determination module 436 may be configured to dim or turn off the lights for a particular area upon a determination that the area is empty (i.e., to conserve energy). Additionally or alternatively, the light adjustment determination module 436 may be configured to illuminate certain portions of the office, as may be determined by a present path of the user (e.g., as may be determinable by a computer 102 worn or otherwise carried by the user).

The health/wellness analysis module 440 is configured to analyze health and wellness related data, such as may be stored in the health information data 406, and provide health and/or wellness recommendations as a result of the analysis. To do so, the illustrative health/wellness analysis module 440 includes a health information profiling module 442, a health information evaluation module 444, and a health/wellness recommendation module 446. The health information profiling module 442 is configured to generate a health profile of the users for which health and/or wellness information has been received or otherwise retrieved, such as from the health information system 118 of FIG. 1 and/or from one or more users via one or more of the computers 102 of FIG. 1, and, in some embodiments, stored in the health information data 406. In some embodiments, the health profiles generated by the health information profiling module 442 may be stored in the health profile data 408.

The health information evaluation module 444 is configured to determine any patterns and/or correlations between a health of a user and light exposure to that user, as compared to the health of other users and light exposure to other users. Accordingly, the health information evaluation module 444 may be configured to determine the patterns and/or correlations from the light data 402, the environment data 404, the health information data 406, and/or the health profile data 408. For example, the health information evaluation module 444 may identify a type of exposure to a particular light for more than a period of time increases the probability of a medical (e.g., debilitating) condition for a certain percentage of users.

The health/wellness recommendation module 446 is configured to determine one or more recommendations to the user, such as based on the patterns and/or correlations determined by the health information evaluation module 444. In other words, depending on a user, or a group of users (e.g., employees in a particular set of cubicles, patients in a room, etc.), the health/wellness recommendation module 446 may determine a particular lighting condition is not conducive to the health the user and/or one or more of the group of users in a particular environment. In some embodiments, the health/wellness recommendation module 446 may be configured to automatically initiate a particular action (i.e., without direction from a user) that results in an adjustment to one or more present lighting conditions of an environment, such as dimming a light, closing a window treatment, etc.

Additionally and/or alternatively, in some embodiments, health/wellness recommendation module 446 may be configured to automatically initiate a passive action that is intended to lead to a manual adjustment to one or more present lighting conditions of an environment. For example, in an office setting, the health/wellness recommendation module 446 may determine that employees working in a particular area (e.g., a floor, a wing, a portion of an area, etc.) with a lighting condition are more susceptible to migraines than other employees working in other areas with different lighting conditions. In such an embodiment, the health/wellness recommendation module 446 may be configured to send a notification to a maintenance department of the company indicating a need to change/upgrade the lighting in the particular area with the lighting condition where more employees are experiencing migraines, which may impact work performance.

In another example, the health/wellness recommendation module 446 may determine lighting conditions at a particular time of day or night are disrupting the sleep of a user. Accordingly, the health/wellness recommendation module 446 may be configured to provide a notification to the user that includes recommendations to improve the lighting conditions based on the source of light contributing to the sub-optimal lighting condition, such as a recommendation to use an alarm clock that emits less light, install blackout curtains for a window to block outside light, etc.

It should be appreciated that, in some embodiments, the health information evaluation module 444 may be configured to generate predictive profiles of future lighting conditions experience for a user or an environment, such as by using the historical data and machine learning algorithms. Accordingly, in such embodiments, future lighting conditions may be identified by the health information evaluation module 444 and addressed by the health/wellness recommendation module 446. For example, a user may request access to light data related to a specific location they intend to visit. In response, the health information evaluation module 444 may analyze historical lighting conditions to determine a predicted lighting condition for the timeframe corresponding to the visit, and the health/wellness recommendation module 446 may provide one or more recommendations to the user based on the lighting condition that the user is anticipated to be exposed to.

Figure 5:
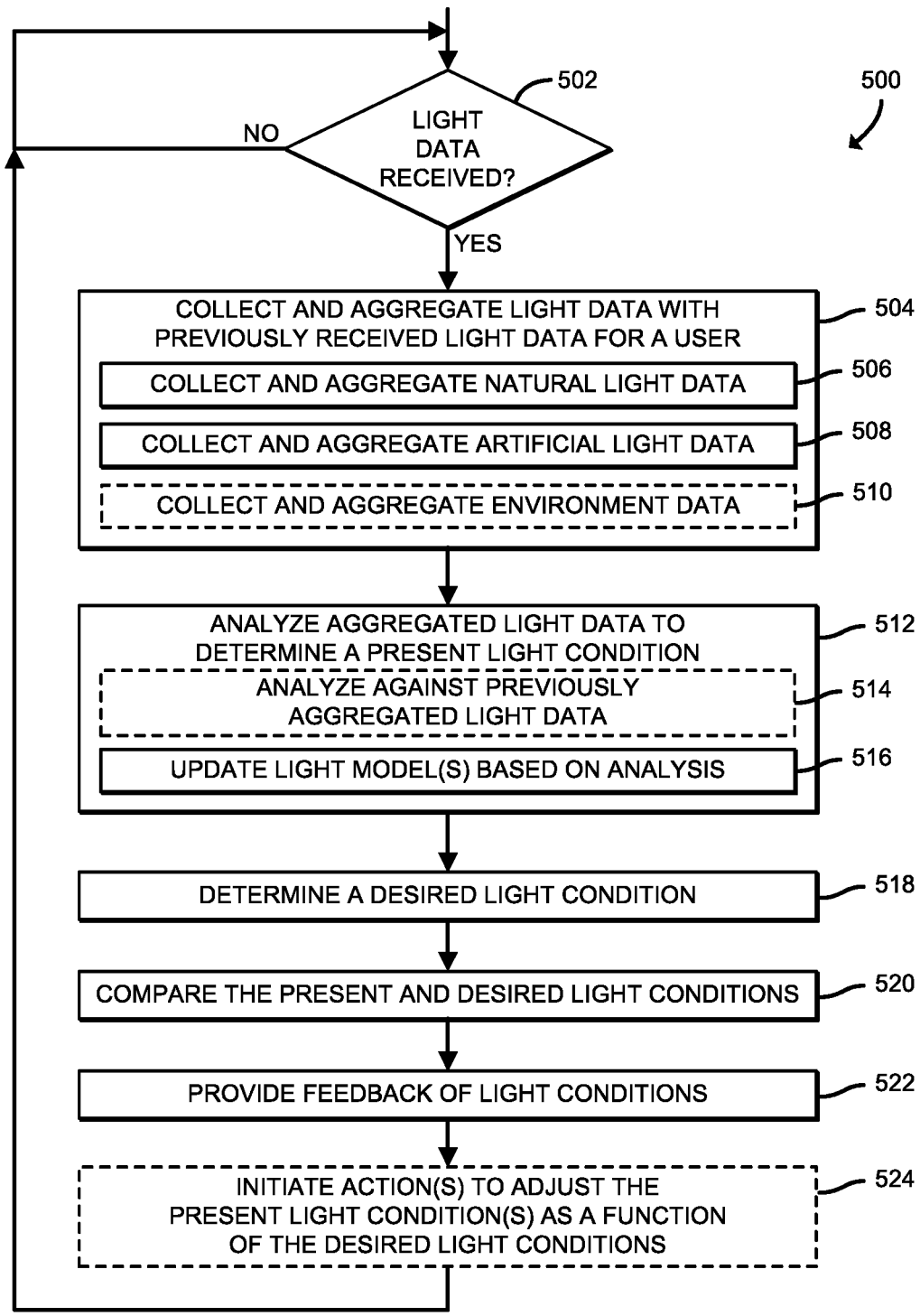
FIG. 5 is a simplified flow diagram of at least one embodiment of a method for analyzing light exposure of an environment that may be executed by the remote computer of FIGS. 3 and 4.

Referring now to FIG. 5, in use, the remote computer 114 may execute a method 500 for analyzing light exposure of an environment (e.g., the environment 110 of FIG. 1). It should be appreciated that at least a portion of method 500 may be embodied as various instructions stored on a computer-readable media, which may be executed by the processor 302, the communication circuitry 310, and/or other components of the remote computer 114 to cause the remote computer 114 to perform the method 500. The computer-readable media may be embodied as any type of media capable of being read by the remote computer 114 including, but not limited to, the memory 306, the data storage device 308, a local memory of a NIC (not shown) of the communication circuitry 310, other memory or data storage devices of the remote computer 114, portable media readable by a peripheral device of the remote computer 114, and/or other media.

The method 500 begins in block 502, in which the remote computer 114 determines whether light data was received. If so, the method 500 advances to block 504, wherein the remote computer 114 collects and aggregates light data with previously received light data for a user (i.e., historical lighting condition data). To do so, in block 506, the remote computer 114 collects and aggregates natural light data (i.e., the portion of the electromagnetic radiation given off by the sun) in the environment, such as may be collected via the one or more light sensors 108 of the computer 102 in environment 110. Additionally, in block 508, the remote computer 114 collects and aggregates artificial light data (i.e., light emitted from incandescent light bulbs, fluorescent tubes, light-emitting diodes, etc., to produce visible light), such as may also be collected via the one or more light sensors 108 of the computer 102 in environment 110. In some embodiments, in block 510, the remote computer 114 additionally collects and aggregates environment data.

In block 512, the remote computer 114 analyzes the aggregated light data to determine a present light condition. In some embodiments, in block 514, the remote computer 114 may additionally analyze the aggregated light data against previously aggregated light data (i.e., historical lighting condition data). It should be appreciated that the remote computer 114 may additionally analyze the aggregated light data against previously aggregated light data for that environment and/or for other environments. In block 516, the remote computer 114 updates one or more light models based on the analysis of the light data. The light models are usable to provide a visual representation of the light data from which various measurements may be based. In block 518, the remote computer 114 determines a desired lighting condition based, at least in part, on the analysis performed in block 512. Such desired lighting conditions may include a one or more desired lighting properties that define the desired lighting condition, such as an amount of natural light, an amount of artificial light, an amount of light directed toward a particular location, etc.

In block 520, the remote computer 114 compares the present light conditions against a desired light condition. It should be appreciated that the desired light condition may be previously determined based on input from the user, such as a mental and/or physical response (e.g., a mood) to particular lighting conditions, and/or a pattern or correlation determined from health information of the user and/or other users as described below. In block 522, the remote computer 114 provides feedback (e.g., models, heat maps, histograms, text, etc.) of the light conditions (e.g., present light conditions, previous light conditions, etc.) to a user (e.g., via a display of the computer 102) for an environment 110. In some embodiment, in block 524, the remote computer 114 is configured to automatically initiate one or more actions to adjust one or more present light conditions as a function of the desired light conditions. As described previously, the one or more actions may include notifying (e.g., via email, text, etc.) maintenance of a sub-optimal lighting condition, automatically dimming a light in the environment, automatically closing a window treatment, and/or any other operation that automatically adjusts a present lighting condition.

Figure 6:
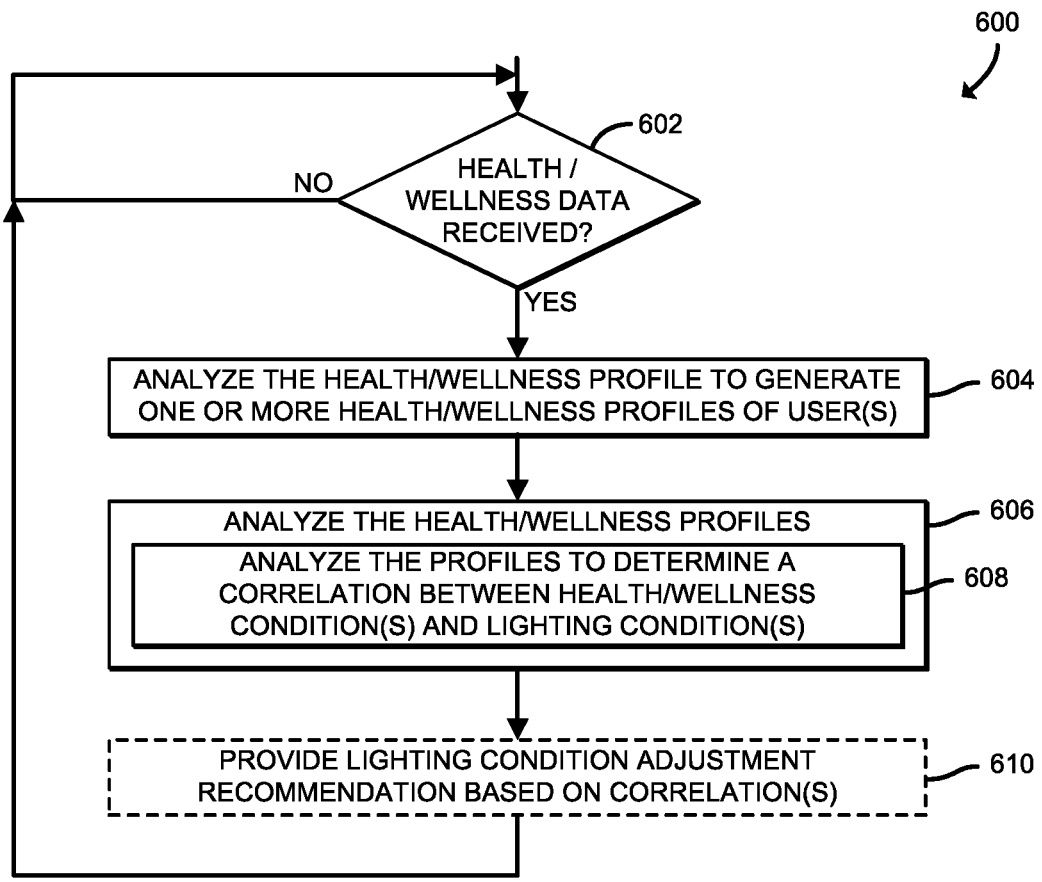
FIG. 6 is a simplified flow diagram of at least one embodiment of a method for analyzing health and wellness data against exposure to light that may be executed by the remote computer of FIGS. 3 and 4.

Referring now to FIG. 6, in use, the remote computer 114 may execute a method 600 for analyzing health and wellness data (i.e., health information) against exposure to light. It should be appreciated that at least a portion of method 600 may be embodied as various instructions stored on a computer-readable media, which may be executed by the processor 302, the communication circuitry 310, and/or other components of the remote computer 114 to cause the remote computer 114 to perform the method 600. The computer-readable media may be embodied as any type of media capable of being read by the remote computer 114 including, but not limited to, the memory 306, the data storage device 308, a local memory of a NIC (not shown) of the communication circuitry 310, other memory or data storage devices of the remote computer 114, portable media readable by a peripheral device of the remote computer 114, and/or other media.

The method 600 begins in block 602, in which the remote computer 114 determines whether light data was received. It should be appreciated that, in some embodiments, the remote computer 114 may be configured to retrieve the health and wellness data. It should be further appreciated that in other embodiments, the remote computer 114 may be additionally or alternatively configured to automatically receive the health and wellness data. If the health and wellness data was received at block 602, the method 600 advances to block 604, wherein the remote computer 114 analyzes the received health and wellness data to generate one or more health and wellness profiles, depending on the number of users corresponding to the health and wellness data received at block 602.

In block 606, the remote computer 114 analyzes the health and wellness profiles. For example, in block 608, the remote computer 114 analyzes the health and wellness profiles to determine a correlation, or pattern, between one or more health and wellness conditions and one or more lighting conditions. In some embodiments, in block 610, the remote computer 114 provides a lighting condition adjustment recommendation based on the determined correlation, or pattern, before the method returns to block 602 to determine whether additional health/wellness data has been received. As described previously, the recommendation is intended to improve, either automatically or passively, one or more present lighting conditions in an environment based on the source of light (i.e., natural light or artificial light) contributing to the sub-optimal lighting condition and the health/wellness condition associated with such lighting conditions and/or one or more users.

EXAMPLES

Illustrative examples of the technologies disclosed herein are provided below. An embodiment of the technologies may include any one or more, and any combination of, the examples described below.

Example 1 includes a remote computer for light exposure analysis, the remote computer comprising a data collection module to receive light data of an environment and a light analysis module to (i) analyze the received light data to determine a present light condition of the environment, wherein the present light condition includes a plurality of present lighting properties that define the present light condition, (ii) compare the present light condition of the environment and a desired lighting condition of the environment, wherein the desired lighting condition includes a plurality of desired lighting properties that define the desired lighting condition, (iii) determine one or more lighting condition adjustments based on the comparison of the present lighting properties of the present light condition and the desired lighting properties of the desired lighting condition, and (iv) initiate one or more actions at the environment based on the lighting condition adjustments.

Example 2 includes the subject matter of Example 1, and wherein one or more of the desired lighting properties of the desired lighting condition are specified by a user.

Example 3 includes the subject matter of any of Examples 1 and 2, and wherein the light analysis module is further to analyze historical lighting condition data to establish one or more desired lighting settings, wherein one or more of the desired lighting properties of the desired lighting condition are determined based on the desired lighting settings.

Example 4 includes the subject matter of any of Examples 1-3, and wherein the light data includes one or more characteristics of the environment, and wherein the one or more characteristics of the environment includes at least one of a time of day, a time zone, a date, a geo-location, an elevation, and a humidity level.

Example 5 includes the subject matter of any of Examples 1-4, and wherein the light data includes one or more characteristics of the user, and wherein the one or more characteristics of the user includes at least one of a gesture performed by the user and a reaction of the user to the present light condition.

Example 6 includes the subject matter of any of Examples 1-5, and wherein the data collection module is further to receive health and wellness data from the user, wherein the health and wellness data includes an effect on the user that corresponds to one or more previous lighting conditions, wherein each of the previous lighting conditions includes a plurality of previous lighting properties, and further comprising a health/wellness analysis module to (i) generate a health profile for the user based on the health and wellness data and (ii) analyze the health profile to determine a correlation between the effect on the user and one or more of the previous lighting properties of the previous lighting conditions.

Example 7 includes the subject matter of any of Examples 1-6, and wherein the light analysis module is further to compare one or more of the present lighting properties of the present lighting condition to a corresponding one of the previous lighting properties correlated to the effect, wherein to determine the lighting condition adjustments further comprises to determine the lighting condition adjustments based on one or more of the present lighting properties being substantially similar to one or more of the corresponding previous lighting properties.

Example 8 includes the subject matter of any of Examples 1-7, and wherein the effect on the user during a previous lighting condition includes at least one of a mental condition affecting the user and a physical condition affecting the user.

Example 9 includes the subject matter of any of Examples 1-8, and wherein the light analysis module is further to provide feedback to a user of the environment, wherein the feedback comprises a result of the comparison of the present light condition of the environment and the desired lighting condition of the environment, and wherein to initiate the one or more actions at the environment are based on an action indication received from the user by the remote computer.

Example 10 includes the subject matter of any of Examples 1-9, and wherein to receive the light data of the environment comprises to receive at least one of a light intensity, a type of light, one or more samples at different frequencies, or a capability of a source of the light data.

Example 11 includes the subject matter of any of Examples 1-10, and wherein to receive the light data of the environment comprises to receive at least one of natural light data and artificial light data.

Example 12 includes the subject matter of any of Examples 1-11, and wherein to receive the light data of the environment further comprises to receive environment data of the environment from a sensor located within the environment, wherein the environment data includes at least one of a position of the sensor, an angle of the sensor, a coordinate of a location of the sensor, a proximity of the sensor to one or more objects obstructing the sensor, a time of day, and a calibration setting.

Example 13 includes the subject matter of any of Examples 1-12, and wherein the present lighting properties include an intensity of light property, and wherein to initiate the action at the environment comprises to initiate an action that adjusts the intensity of light property.

Example 14 includes the subject matter of any of Examples 1-13, and wherein to initiate the action at the environment based on the lighting condition adjustments comprises to initiate the action without direction from a user.

Example 15 includes the subject matter of any of Examples 1-14, and wherein to initiate the action at the environment based on the lighting condition adjustments comprises to initiate the action in response to a user interaction.

Example 16 includes the subject matter of any of Examples 1-15, and wherein to initiate the one or more actions comprises to one of notify maintenance of the environment of a sub-optimal lighting condition, automatically dim a light source in the environment, and automatically close a window treatment.

Example 17 includes a method for light exposure analysis, the method comprising receiving, by a remote computer, light data of an environment from one or more computers in the environment, wherein the light data is indicative of one or more properties of light detected in the environment; analyzing, by the remote computer, the received light data to determine a present light condition of the environment, wherein the present light condition includes a plurality of present lighting properties that define the present light condition; comparing, by the remote computer, the present light condition of the environment and a desired lighting condition of the environment, wherein the desired lighting condition includes a plurality of desired lighting properties that define the desired lighting condition; determining, by the remote computer, one or more lighting condition adjustments based on the comparison of the present lighting properties of the present light condition and the desired lighting properties of the desired lighting condition; and initiating, by the remote computer, one or more actions based on the lighting condition adjustments.

Example 18 includes the subject matter of Example 17, and further comprising receiving the one or more of the desired lighting properties of the desired lighting condition from a user of the computer.

Example 19 includes the subject matter of any of Examples 17 and 18, and further comprising analyzing, by the remote computer, historical lighting condition data to establish one or more desired lighting settings, wherein one or more of the desired lighting properties of the desired lighting condition are determined based on the desired lighting settings.

Example 20 includes the subject matter of any of Examples 17-19, and wherein receiving the light data includes receiving one or more characteristics of the environment, and wherein the one or more characteristics of the environment include at least one of a time of day, a time zone, a date, a geo-location, an elevation, and a humidity level.

Example 21 includes the subject matter of any of Examples 17-20, and further comprising receiving, by the remote computer, health and wellness data from the user, wherein the health and wellness data includes an effect on the user that corresponds to one or more previous lighting conditions, wherein each of the previous lighting conditions includes a plurality of previous lighting properties, generating, by the remote computer, a health profile for the user based on the health and wellness data, and analyzing, by the remote computer, the health profile to determine a correlation between the effect on the user and one or more of the previous lighting properties of the previous lighting conditions.

Example 22 includes the subject matter of any of Examples 17-21, and further comprising comparing, by the remote computer, one or more of the present lighting properties of the present lighting condition to a corresponding one of the previous lighting properties correlated to the effect, wherein determining the lighting condition adjustments further comprises determining the lighting condition adjustments based on one or more of the present lighting properties being substantially similar to one or more of the corresponding previous lighting properties.

Example 23 includes the subject matter of any of Examples 17-22, and wherein receiving the effect on the user comprises receiving at least one of a mental condition affecting the user and a physical condition affecting the user.

Example 24 includes the subject matter of any of Examples 17-23, and further comprising providing feedback to a user of the environment, wherein the feedback comprises a result of the comparison of the present light condition of the environment and the desired lighting condition of the environment, and wherein initiating the one or more actions at the environment are based on an action indication received from the user by the remote computer.

Example 25 includes the subject matter of any of Examples 17-24, and wherein receiving the light data of the environment comprises receiving at least one of a light intensity, a type of light, one or more samples at different frequencies, or a capability of a source of the light data.

Example 26 includes the subject matter of any of Examples 17-25, and wherein receiving the light data of the environment comprises receiving at least one of natural light data and artificial light data.

Example 27 includes the subject matter of any of Examples 17-26, and wherein receiving the light data of the environment further comprises receiving environment data of the environment from a sensor located within the environment, wherein the environment data includes at least one of a position of the sensor, an angle of the sensor, a coordinate of a location of the sensor, a proximity of the sensor to one or more objects obstructing the sensor, a time of day, and a calibration setting.

Example 28 includes the subject matter of any of Examples 17-27, and wherein analyzing the present lighting properties includes analyzing an intensity of light property, and wherein initiating the action at the environment comprises initiating an action that adjusts the intensity of light property.

Example 29 includes the subject matter of any of Examples 17-28, and wherein initiating the action at the environment based on the lighting condition adjustments comprises initiating the action without direction from a user.

Example 30 includes the subject matter of any of Examples 17-29, and wherein initiating the action at the environment based on the lighting condition adjustments comprises initiating the action in response to a user interaction.

Example 31 includes the subject matter of any of Examples 17-30, and wherein initiating the one or more actions comprises one of notifying maintenance of the environment of a sub-optimal lighting condition, automatically dimming a light source in the environment, automatically brightening a light source in the environment, and automatically closing a window treatment.

Example 32 includes a destination computing device comprising a processor and a memory having stored therein a plurality of instructions that when executed by the processor cause the destination computing device to perform the method of any of Examples 17-31.

Example 33 includes one or more machine readable storage media comprising a plurality of instructions stored thereon that in response to being executed result in a destination computing device performing the method of any of Examples 17-31.

Example 34 includes a destination computing device for light exposure analysis, the destination computing device comprising means for receiving light data of an environment from one or more computers in the environment, wherein the light data is indicative of one or more properties of light detected in the environment, means for analyzing the received light data to determine a present light condition of the environment, wherein the present light condition includes a plurality of present lighting properties that define the present light condition, means for comparing the present light condition of the environment and a desired lighting condition of the environment, wherein the desired lighting condition includes a plurality of desired lighting properties that define the desired lighting condition, means for determining one or more lighting condition adjustments based on the comparison of the present lighting properties of the present light condition and the desired lighting properties of the desired lighting condition, and means for initiating one or more actions based on the lighting condition adjustments.

Example 35 includes the subject matter of Example 34, and further comprising means for receiving the one or more of the desired lighting properties of the desired lighting condition from a user of the computer.

Example 36 includes the subject matter of Examples 34 and 35, and further comprising means for analyzing historical lighting condition data to establish one or more desired lighting settings, wherein one or more of the desired lighting properties of the desired lighting condition are determined based on the desired lighting settings.

Example 37 includes the subject matter of any of Examples 34-36, and wherein the means for receiving the light data comprises means for receiving one or more characteristics of the environment, and wherein the one or more characteristics of the environment include at least one of a time of day, a time zone, a date, a geo-location, an elevation, and a humidity level.

Example 38 includes the subject matter of any of Examples 34-37, and further comprising means for receiving health and wellness data from the user, wherein the health and wellness data includes an effect on the user that corresponds to one or more previous lighting conditions, wherein each of the previous lighting conditions includes a plurality of previous lighting properties, means for generating a health profile for the user based on the health and wellness data, and means for analyzing the health profile to determine a correlation between the effect on the user and one or more of the previous lighting properties of the previous lighting conditions.

Example 39 includes the subject matter of any of Examples 34-38, and further comprising means for comparing one or more of the present lighting properties of the present lighting condition to a corresponding one of the previous lighting properties correlated to the effect, wherein the means for determining the lighting condition adjustments further comprises means for determining the lighting condition adjustments based on one or more of the present lighting properties being substantially similar to one or more of the corresponding previous lighting properties.

Example 40 includes the subject matter of any of Examples 34-39, and wherein the means for receiving the effect on the user comprises means for receiving at least one of a mental condition affecting the user and a physical condition affecting the user.

Example 41 includes the subject matter of any of Examples 34-40, and further comprising means for providing feedback to a user of the environment, wherein the feedback comprises a result of the comparison of the present light condition of the environment and the desired lighting condition of the environment, and wherein the means for initiating the one or more actions at the environment are based on an action indication received from the user by the remote computer.

Example 42 includes the subject matter of any of Examples 34-41, and wherein the means for receiving the light data of the environment comprises means for receiving at least one of a light intensity, a type of light, one or more samples at different frequencies, or a capability of a source of the light data.

Example 43 includes the subject matter of any of Examples 34-42, and wherein the means for receiving the light data of the environment comprises means for receiving at least one of natural light data and artificial light data.

Example 44 includes the subject matter of any of Examples 34-43, and wherein the means for receiving the light data of the environment further comprises means for receiving environment data of the environment from a sensor located within the environment, wherein the environment data includes at least one of a position of the sensor, an angle of the sensor, a coordinate of a location of the sensor, a proximity of the sensor to one or more objects obstructing the sensor, a time of day, and a calibration setting.

Example 45 includes the subject matter of any of Examples 34-44, and wherein the means for analyzing the present lighting properties comprises means for analyzing an intensity of light property, and wherein initiating the action at the environment comprises initiating an action that adjusts the intensity of light property.

Example 46 includes the subject matter of any of Examples 34-45, and wherein the means for initiating the action at the environment based on the lighting condition adjustments comprises initiating the action without direction from a user.

Example 47 includes the subject matter of any of Examples 34-46, and wherein the means for initiating the action at the environment based on the lighting condition adjustments comprises means for initiating the action in response to a user interaction.

Example 48 includes the subject matter of any of Examples 34-47, and wherein the means for initiating the one or more actions comprises at least one or means for notifying maintenance of the environment of a sub-optimal lighting condition, means for automatically dimming a light source in the environment, means for automatically brightening a light source in the environment, and means for automatically closing a window treatment.

The invention claimed is:

1. A remote computer for light exposure analysis, the remote computer comprising:
   a data collection module to (i) receive light data of an environment and (ii) receive health and wellness data from the user, wherein the health and wellness data includes an effect on the user that corresponds to one or more previous lighting conditions previously collected by the data collection module, wherein each of the previous lighting conditions includes a plurality of previous lighting properties;
   a health/wellness analysis module to (i) generate a health profile for the user based on the health and wellness data received from the user and one or more of the previous lighting properties of the previous lighting conditions, wherein the health profile associates each effect on the user with a corresponding one or more previous lighting properties and (ii) analyze the health profile to determine any correlations between the effect on the user and one or more of the previous lighting properties of the previous lighting conditions; and
   a light analysis module to:
      analyze the received light data to determine a present light condition of the environment and a physical gesture performed by the user in response to the present light condition, wherein the present light condition includes a plurality of present lighting properties that define the present light condition,
      determine whether the present light condition is indicative of one or more adverse health effects as a function of the determined correlations, the present light condition, and the physical gesture performed by the user,
      determine, in response to a determination the present light condition is indicative of the one or more adverse health effects, a desired lighting condition of the environment as a function of the present light condition and the one or more adverse health effects on the user, wherein the desired lighting condition includes a plurality of desired lighting properties that define the desired lighting condition,
      determine one or more lighting condition adjustments based on the present lighting properties of the present light condition relative to the desired lighting properties of the desired lighting condition, and
      initiate one or more actions at the environment based on the lighting condition adjustments, wherein to initiate the one or more actions includes to automatically adjust at least one light source in the environment.

2. The remote computer of claim 1, wherein the light analysis module is further to analyze historical lighting condition data to establish one or more desired lighting settings, wherein one or more of the desired lighting properties of the desired lighting condition are determined based on the desired lighting settings.

3. The remote computer of claim 1, wherein the light data includes one or more characteristics of the environment, and wherein the one or more characteristics of the environment includes at least one of a time of day, a time zone, a date, a geo-location, an elevation, and a humidity level.

4. The remote computer of claim 1, wherein the light analysis module is further to compare one or more of the present lighting properties of the present lighting condition to a corresponding one of the previous lighting properties correlated to the effect, wherein to determine the lighting condition adjustments further comprises to determine the lighting condition adjustments based on one or more of the present lighting properties being substantially similar to one or more of the corresponding previous lighting properties.

5. The remote computer of claim 1, wherein the light analysis module is further to provide feedback to a user of the environment, wherein the feedback comprises a result of the comparison of the present light condition of the environment and the desired lighting condition of the environment, and wherein to initiate the one or more actions at the environment are based on an action indication received from the user by the remote computer.

6. The remote computer of claim 1, wherein to receive the light data of the environment comprises to receive at least one of a light intensity, a type of light, one or more samples at different frequencies, or a capability of a source of the light data.

7. The remote computer of claim 6, wherein to receive the light data of the environment further comprises to receive environment data of the environment from a sensor located within the environment, wherein the environment data includes at least one of a position of the sensor, an angle of the sensor, a coordinate of a location of the sensor, a proximity of the sensor to one or more objects obstructing the sensor, a time of day, and a calibration setting.

8. The remote computer of claim 1, wherein to initiate the one or more actions comprises to one of notify maintenance of the environment of a sub-optimal lighting condition, automatically dim a light source in the environment, automatically brighten a light source in the environment, and automatically close a window treatment.

9. One or more non-transitory, machine-readable storage media comprising a plurality of instructions stored thereon that, in response to execution by a remote computer, cause the remote computer to:
receive health and wellness data from the user, wherein the health and wellness data includes an effect on the user that corresponds to one or more previous lighting conditions previously collected by the data collection module, wherein each of the previous lighting conditions includes a plurality of previous lighting properties;
generate a health profile for the user based on the health and wellness data received from the user and one or more of the previous lighting properties of the previous lighting conditions, wherein the health profile associates each effect on the user with a corresponding one or more previous lighting properties;
analyze the health profile to determine any correlations between the effect on the user and one or more of the previous lighting properties of the previous lighting conditions;
receive light data of an environment;
analyze the received light data to determine a present light condition of the environment and a physical gesture performed by the user in response to the present light condition, wherein the present light condition includes a plurality of present lighting properties that define the present light condition;
determine whether the present light condition is indicative of one or more adverse health effects as a function of the determined correlations, the present light condition, and the physical gesture performed by the user;
determine, in response to a determination the present light condition is indicative of the one or more adverse health effects, a desired lighting condition of the environment as a function of the present light condition and the one or more adverse health effects on the user, wherein the desired lighting condition includes a plurality of desired lighting properties that define the desired lighting condition;
determine one or more lighting condition adjustments based on the present lighting properties of the present light condition relative to the desired lighting properties of the desired lighting condition; and
initiate one or more actions at the environment based on the lighting condition adjustments, wherein to initiate the one or more actions includes to automatically adjust at least one light source in the environment.

10. The one or more non-transitory, machine-readable storage media of claim 9, wherein the plurality of instruction further cause the remote computer to analyze historical lighting condition data to establish one or more desired lighting settings, wherein one or more of the desired lighting properties of the desired lighting condition are determined based on the desired lighting settings.

11. The one or more non-transitory, machine-readable storage media of claim 9, wherein the light data includes one or more characteristics of the environment, and wherein the one or more characteristics of the environment includes at least one of a time of day, a time zone, a date, a geo-location, an elevation, and a humidity level.

12. The one or more non-transitory, machine-readable storage media of claim 9, wherein the plurality of instruction further cause the remote computer to compare one or more of the present lighting properties of the present lighting condition to a corresponding one of the previous lighting properties correlated to the effect, wherein to determine the lighting condition adjustments further comprises to determine the lighting condition adjustments based on one or more of the present lighting properties being substantially similar to one or more of the corresponding previous lighting properties.

13. The one or more non-transitory, machine-readable storage media of claim 9, wherein the plurality of instruction further cause the remote computer to provide feedback to a user of the environment, wherein the feedback comprises a result of the comparison of the present light condition of the environment and the desired lighting condition of the environment, and wherein to initiate the one or more actions at the environment are based on an action indication received from the user by the remote computer.

14. The one or more non-transitory, machine-readable storage media of claim 9, wherein to receive the light data of the environment comprises to receive at least one of a light intensity, a type of light, one or more samples at different frequencies, or a capability of a source of the light data.

15. The one or more non-transitory, machine-readable storage media of claim 14, wherein to receive the light data of the environment further comprises to receive environment data of the environment from a sensor located within the environment, wherein the environment data includes at least one of a position of the sensor, an angle of the sensor, a coordinate of a location of the sensor, a proximity of the sensor to one or more objects obstructing the sensor, a time of day, and a calibration setting.

16. The one or more non-transitory, machine-readable storage media of claim 9, wherein to initiate the one or more actions comprises to one of notify maintenance of the environment of a sub-optimal lighting condition, automatically dim a light source in the environment, automatically brighten a light source in the environment, and automatically close a window treatment.

17. A method for light exposure analysis, the method comprising:
 receiving, by the remote computer, health and wellness data from the user, wherein the health and wellness data includes an effect on the user that corresponds to one or more previous lighting conditions previously collected by the data collection module, wherein each of the previous lighting conditions includes a plurality of previous lighting properties;
 generating, by the remote computer, a health profile for the user based on the health and wellness data received from the user and one or more of the previous lighting properties of the previous lighting conditions, wherein the health profile associates each effect on the user with a corresponding one or more previous lighting properties;
 analyzing, by the remote computer, the health profile to determine any correlations between the effect on the user and one or more of the previous lighting properties of the previous lighting conditions;
 receiving, by a remote computer, light data of an environment from one or more computers in the environment, wherein the light data is indicative of one or more properties of light detected in the environment;
 analyzing, by the remote computer, the received light data to determine a present light condition of the environment and a physical gesture performed by the user in response to the present light condition, wherein the present light condition includes a plurality of present lighting properties that define the present light condition;
 determining, by the remote computer, whether the present light condition is indicative of one or more adverse health effects as a function of the determined correlations, the present light condition, and the physical gesture performed by the user;
 determining, by the remote computer and in response to a determination the present light condition is indicative of the one or more adverse health effects, a desired lighting condition of the environment as a function of the present light condition, the one or more adverse health effects on the user, wherein the desired lighting condition includes a plurality of desired lighting properties that define the desired lighting condition;
 determining, by the remote computer, one or more lighting condition adjustments based on the present lighting properties of the present light condition relative to the desired lighting properties of the desired lighting condition; and
 initiating, by the remote computer, one or more actions based on the lighting condition adjustments, wherein initiating the one or more actions includes to automatically adjust at least one light source in the environment.

18. The method of claim 17, further comprising analyzing, by the remote computer, historical lighting condition data to establish one or more desired lighting settings, wherein one or more of the desired lighting properties of the desired lighting condition are determined based on the desired lighting settings.

19. The method of claim 17, further comprising comparing, by the remote computer, one or more of the present lighting properties of the present lighting condition to a corresponding one of the previous lighting properties correlated to the effect, wherein determining the lighting condition adjustments further comprises determining the lighting condition adjustments based on one or more of the present lighting properties being substantially similar to one or more of the corresponding previous lighting properties.

20. The method of claim 17, further comprising providing feedback to a user of the environment, wherein the feedback comprises a result of the comparison of the present light condition of the environment and the desired lighting condition of the environment, and wherein initiating the one or more actions at the environment are based on an action indication received from the user by the remote computer.

* * * * *